(12) United States Patent
Hashmi et al.

(10) Patent No.: US 9,481,679 B2
(45) Date of Patent: Nov. 1, 2016

(54) PROCESS FOR THE PREPARATION OF TOFACITINIB AND INTERMEDIATES THEREOF

(71) Applicant: SUN PHARMACEUTICAL INDUSTRIES LIMITED, Mumbai, Maharashtra (IN)

(72) Inventors: Mohammed Salman Hashmi, Aligarh (IN); Yoginder Pal Sachdeva, Faridabad (IN); Chandra Has Khanduri, Gurgaon (IN)

(73) Assignee: SUN PHARMACEUTICAL INDUSTRIES LIMITED, Mumbai (IN)

( * ) Notice: Subject to any disclaimer, the term of this patent is extended or adjusted under 35 U.S.C. 154(b) by 0 days.

(21) Appl. No.: 14/652,474

(22) PCT Filed: Dec. 17, 2013

(86) PCT No.: PCT/IB2013/061046
§ 371 (c)(1),
(2) Date: Jun. 16, 2015

(87) PCT Pub. No.: WO2014/097150
PCT Pub. Date: Jun. 26, 2014

(65) Prior Publication Data
US 2015/0322072 A1 Nov. 12, 2015

(30) Foreign Application Priority Data
Dec. 17, 2012 (IN) ............................ 3898/DEL/2012

(51) Int. Cl.
| C07D 211/56 | (2006.01) |
| C07D 487/04 | (2006.01) |
| C07D 213/74 | (2006.01) |
| C07D 213/61 | (2006.01) |
| C07D 471/04 | (2006.01) |

(52) U.S. Cl.
CPC ........... *C07D 487/04* (2013.01); *C07D 211/56* (2013.01); *C07D 213/61* (2013.01); *C07D 213/74* (2013.01); *C07D 471/04* (2013.01)

(58) Field of Classification Search
CPC ... C07D 213/61; C07D 211/56; C07D 213/74; C07D 487/04; C07D 471/04
USPC ........................................................ 546/184
See application file for complete search history.

(56) References Cited

U.S. PATENT DOCUMENTS

| 5,733,912 A | 3/1998 | Wasicak et al. ............... 514/253 |
| 6,696,567 B2 | 2/2004 | Blumenkopf et al. ........ 544/280 |
| 6,965,027 B2 | 11/2005 | Flanagan et al. ............. 544/280 |
| 7,084,277 B2 | 8/2006 | Ripin ............................ 546/244 |
| 7,301,023 B2 | 11/2007 | Flanagan et al. ............. 544/280 |
| 7,456,192 B2 | 11/2008 | Imbert et al. ................ 514/279 |
| RE41,783 E | 9/2010 | Blumenkopf et al. ..... 514/265.1 |
| 2004/0102627 A1* | 5/2004 | Ripin .................. C07D 211/42 544/60 |
| 2007/0078135 A1 | 4/2007 | Yuan et al. .................... 514/241 |
| 2010/0291026 A1* | 11/2010 | Rao ...................... C07D 487/04 424/85.2 |
| 2011/0165183 A1* | 7/2011 | Babu ................... C07D 471/04 424/184.1 |
| 2012/0034250 A1* | 2/2012 | Shirakami ........... C07D 471/14 424/184.1 |

FOREIGN PATENT DOCUMENTS

| CN | 100460394 | 2/2009 | ........... C07D 213/73 |
| EP | 2 420 502 | 2/2012 | ........... C07D 471/14 |
| JP | 08208609 | * 8/1996 | |
| WO | WO 2007/012953 | 2/2007 | ........... C07D 487/04 |
| WO | WO 2012/135338 | 10/2012 | ........... C07D 487/04 |

OTHER PUBLICATIONS

Muthukumar; Indian Journal of Chemistry, Section B, 2012, 51, 388-392.*
Walker; Journal of Organic Chemistry 1961, 26, 2740-2747.*
Cai et al., "Investigation of Practical Routes for the Kilogram-Scale Production of cis-3-Methylamino-4-methylpiperidines," *Organic Process Research & Development*, 9(1):51-56 (2005).
Srivastava, "Assessment of the Catalytic Activities of Novel Brönsted Acidic Ionic Liquid Catalysts," *Catalysis Letters*, 139(1-2):17-25 (2010).

(Continued)

*Primary Examiner* — Noble Jarrell
*Assistant Examiner* — Daniel Carcanague

(57) ABSTRACT

The present invention provides compounds of Formula III and Formula VI, and processes for their preparation. The present invention further provides use of the compounds of Formula III and Formula VI for the preparation of tofacitinib or isomers or a mixture of isomers or salts thereof.

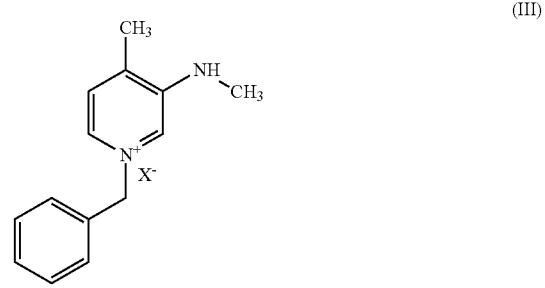

(III)

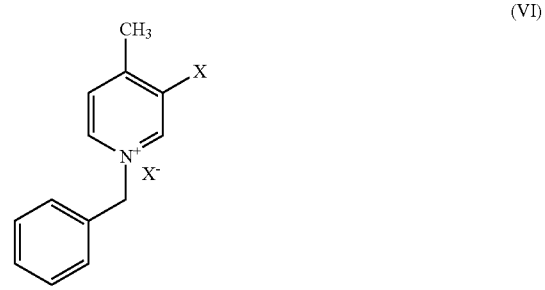

(VI)

16 Claims, No Drawings

(56) References Cited

OTHER PUBLICATIONS

Jiao et al., "A Facile and Practical Copper Powder-Catalyzed, Organic Solvent- and Ligand-Free Ullmann Amination of Aryl Halides," *Journal of Organic Chemistry*, 76(4):1180-1183 (2011).
Flanagan et al., "Discovery of CP-690,550: A Potent and Selective Janus Kinase (JAK) Inhibitor for the Treatment of Autoimmune Diseases and Organ Transplant Rejection," *Journal of Medicinal Chemistry*, 53(24):8468-8484 (2010).
Robert-Piessard et al., "Non-acidic anti-inflammatory compounds: activity of N-(4,6-dimethyl-2-pyridinyl) benzamides and derivatives," *European Journal of Medicinal Chemistry*, 25(1):9-19 (1990).

* cited by examiner

PROCESS FOR THE PREPARATION OF TOFACITINIB AND INTERMEDIATES THEREOF

FIELD OF THE INVENTION

The present invention provides compounds of Formula II, Formula III, and Formula VI, and processes for their preparation. The present invention further provides use of the compounds of Formula II, Formula III, and Formula VI for the preparation of tofacitinib or isomers or a mixture of isomers or salts thereof.

BACKGROUND OF THE INVENTION

Tofacitinib chemically is 3-{(3R,4R)-4-methyl-3-[methyl (7H-pyrrolo[2,3-d]pyrimidin-4-yl)amino]piperidin-1-yl}-3-oxopropanenitrile of Formula I.

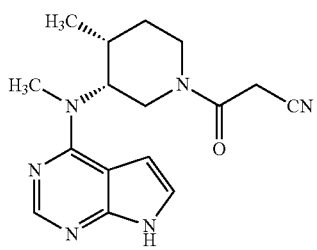

Formula I

Tofacitinib is a Janus kinase 3 (JAK3) inhibitor.

U.S. Pat. No. RE41,783 provides a process for the preparation of a tofacitinib intermediate, (1-benzyl-4-methylpiperidin-3-yl)-methylamine, wherein 1-benzyl-4-methylpiperidin-3-one is stirred with methylamine in the presence of acetic acid for 16 hours at room temperature, then the mixture obtained is further stirred with triacetoxy sodium borohydride for 24 hours to provide (1-benzyl-4-methylpiperidin-3-yl)-methylamine. The amination process described in U.S. Pat. No. RE41,783 is a two-step process, wherein an imine intermediate is first formed in situ by the reaction between 1-benzyl-4-methylpiperidin-3-one and methylamine. This imine intermediate on treatment with triacetoxy sodium borohydride provides (1-benzyl-4-methylpiperidin-3-yl)-methylamine. This process involves long reaction hours and costly reagents, for example, triacetoxy sodium borohydride.

U.S. Pat. No. 6,696,567 provides a process involving six steps for the preparation of (1-benzyl-4-methylpiperidin-3-yl)-methylamine starting from 4-methylpyridine and benzylchloride. The process provided therein involves the use of costly and corrosive reagents, for example, borontrifluoride etherate, hydrogen peroxide, and triacetoxy sodium borohydride.

U.S. Pat. No. 7,084,277 provides a process involving four steps for the preparation of (1-benzyl-4-methylpiperidin-3-yl)-methylamine starting from 4-methyl-pyridin-3-ylamine. The process provided therein involves the use of costly starting material and/or reagents, for example, 4-methyl-pyridin-3-ylamine, rhodium on alumina and sodium triacetoxyborohydride.

The prior art processes for the preparation of (1-benzyl-4-methylpiperidin-3-yl)-methylamine involve a number of reaction steps and make use of costly and corrosive starting materials and/or reagents. Accordingly, these processes are not suitable at an industrial scale. Therefore, there is still a need in the art to develop an economically attractive process for the preparation of (1-benzyl-4-methylpiperidin-3-yl)-methylamine.

SUMMARY OF THE INVENTION

The present inventors have developed an economically attractive and environmentally friendly process for the preparation of (1-benzyl-4-methylpiperidin-3-yl)-methylamine. The process of the present invention involves the use of less expensive chemicals and reagents, fewer reaction steps in the reaction sequence, and reduced reaction times.

The present invention provides compounds of Formula II, Formula III, and Formula VI, and processes for their preparation. The present invention further provides the use of the compounds of Formula II, Formula III, and Formula VI for the preparation of tofacitinib or isomers or a mixture of isomers or salts thereof.

DETAILED DESCRIPTION OF THE INVENTION

A first aspect of the present invention provides a process for the preparation of a compound of Formula II

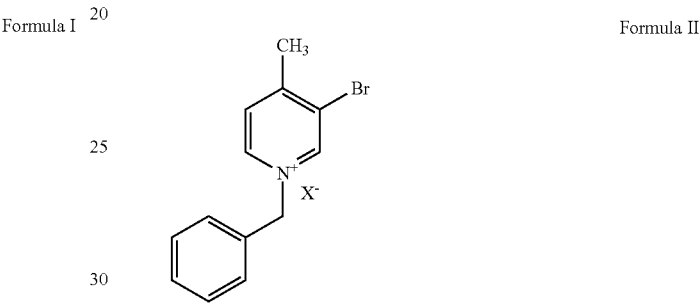

Formula II comprising treating 3-bromo-4-methylpyridine with benzyl halide,
wherein $X^-$ is $Cl^-$, $Br^-$, or $I^-$.

A second aspect of the present invention provides a process for the preparation of a compound of Formula III

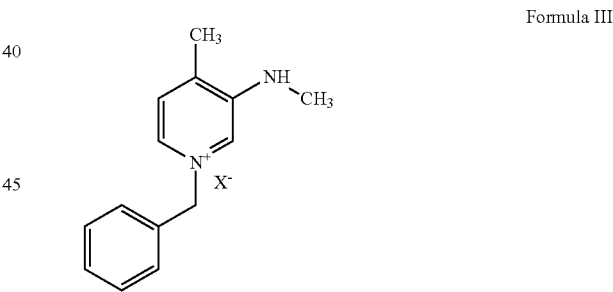

Formula III comprising the steps of:
a) treating 3-bromo-4-methylpyridine with benzyl halide to obtain a compound of Formula II; and

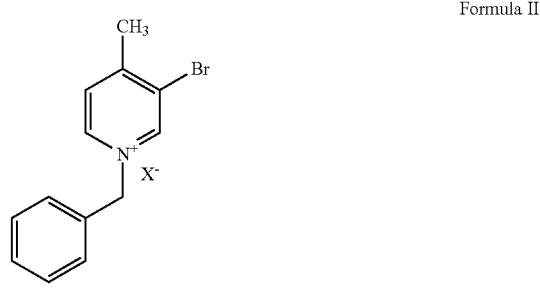

Formula II b) treating the compound of Formula II with methylamine to obtain the compound of Formula III, wherein X⁻ is Cl⁻, Br⁻, or I⁻.

A third aspect of the present invention provides a process for the preparation of a compound of Formula III

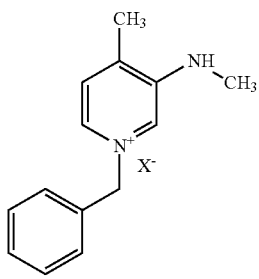

Formula III comprising treating a compound of Formula II

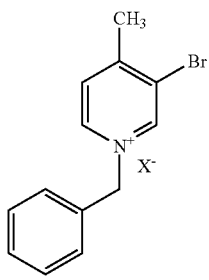

Formula II with methylamine to obtain the compound of Formula III, wherein X⁻ is Cl⁻, Br⁻, or I⁻.

A fourth aspect of the present invention provides a process for the preparation of a compound of Formula IV

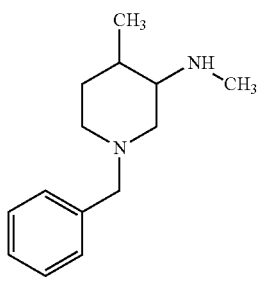

Formula IV wherein the process comprises the steps of:
a) treating 3-bromo-4-methylpyridine with benzyl halide to obtain a compound of Formula II;

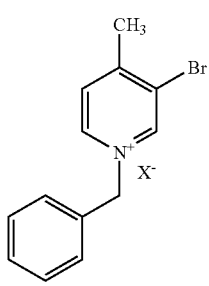

Formula II b) treating the compound of Formula II with methylamine to obtain a compound of Formula III; and

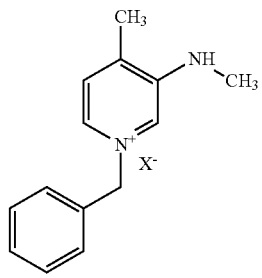

Formula III c) reducing the compound of Formula III to obtain the compound of Formula IV,
wherein X⁻ is Cl⁻, Br⁻, or I⁻.

A fifth aspect of the present invention provides a process for the preparation of a compound of Formula IV

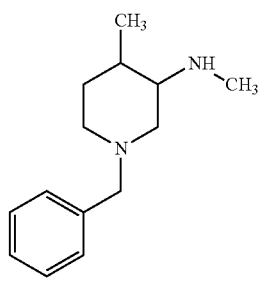

Formula IV wherein the process comprises the steps of:
a) treating a compound of Formula II

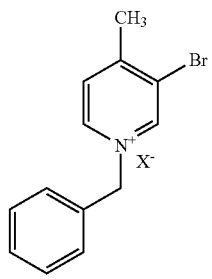

Formula II with methylamine to obtain a compound of Formula III; and

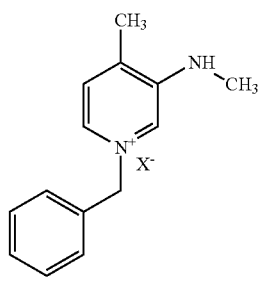

Formula III b) reducing the compound of Formula III to obtain the compound of Formula IV,
wherein X⁻ is Cl⁻, Br⁻, or I⁻.

A sixth aspect of the present invention provides a process for the preparation of a compound of Formula IV

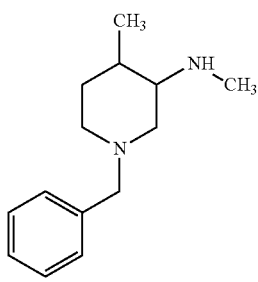

Formula IV wherein the process comprises reducing a compound of Formula III

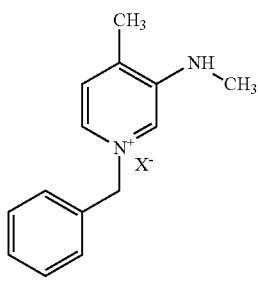

Formula III to obtain the compound of Formula IV,
wherein X⁻ is Cl⁻, Br⁻, or I⁻.

A seventh aspect of the present invention provides a process for the preparation of a compound of Formula VI

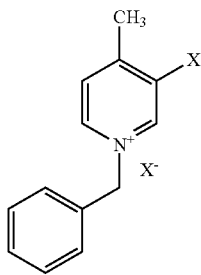

Formula VI comprising treating a compound of Formula V

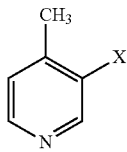

Formula V with benzyl halide to obtain the compound of Formula VI,
wherein X is Cl, Br, or I, and X⁻ is Cl⁻, Br⁻, or I⁻.

An eighth aspect of the present invention provides a process for the preparation of a compound of Formula III

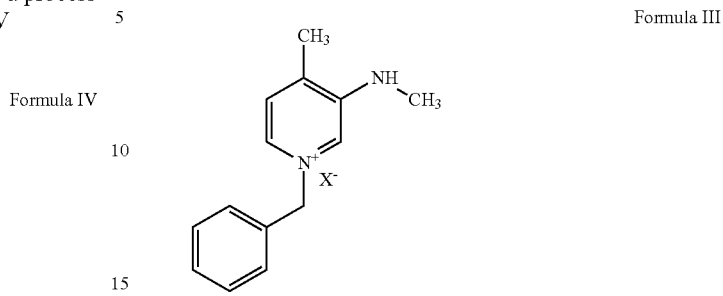

Formula III comprising the steps of:
a) treating a compound of Formula V

Formula V with benzyl halide to obtain a compound of Formula VI; and

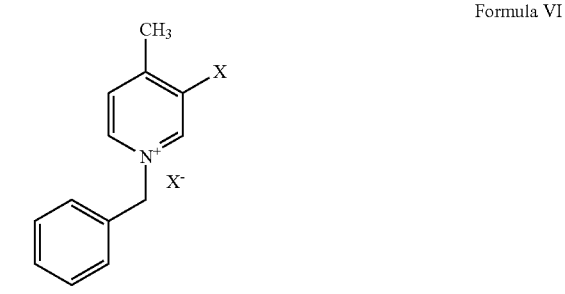

Formula VI b) treating the compound of Formula VI with methylamine to obtain the compound of Formula III,
wherein X is Cl, Br, or I, and X⁻ is Cl⁻, Br⁻, or I⁻.

A ninth aspect of the present invention provides a process for the preparation of a compound of Formula III

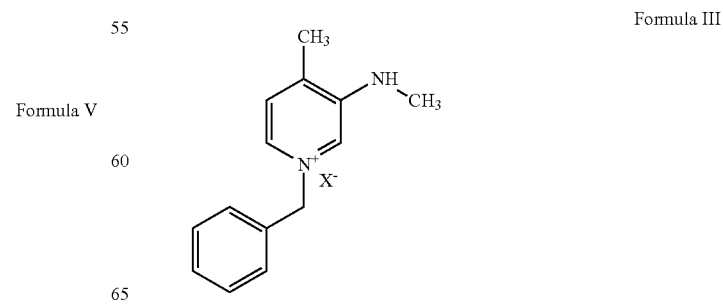

Formula III comprising treating a compound of Formula VI

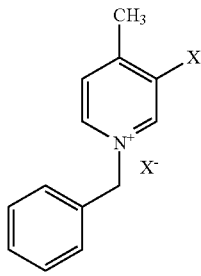

Formula VI with methylamine to obtain the compound of Formula III, wherein X is Cl, Br, or I, and X⁻ is Cl⁻, Br⁻, or I⁻.

A tenth aspect of the present invention provides a process for the preparation of a compound of Formula IV

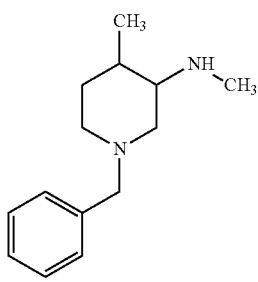

Formula IV wherein the process comprises the steps of:
a) treating a compound of Formula V

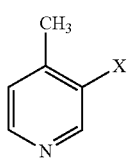

Formula V with benzyl halide to obtain a compound of Formula VI;

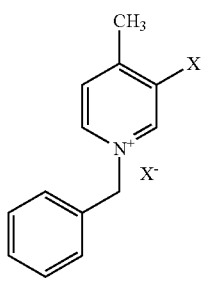

Formula VI b) treating the compound of Formula VI with methylamine to obtain a compound of Formula III; and

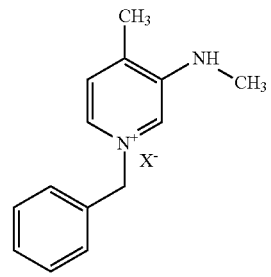

Formula III c) reducing the compound of Formula III to obtain the compound of Formula IV,
wherein X is Cl, Br, or I, and X⁻ is Cl⁻, Br⁻, or I⁻.

An eleventh aspect of the present invention provides a process for the preparation of a compound of Formula IV

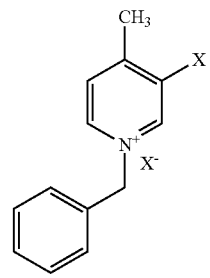

Formula IV wherein the process comprises the steps of:
a) treating a compound of Formula VI

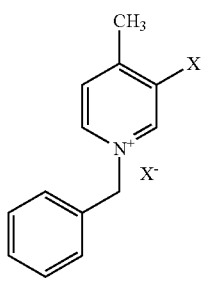

Formula VI with methylamine to obtain a compound of Formula III; and

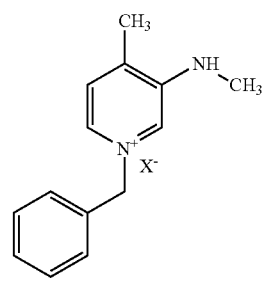

Formula III b) reducing the compound of Formula III to obtain the compound of Formula IV, wherein X is Cl, Br, or I, and X⁻ is Cl⁻, Br⁻, or I⁻.

A twelfth aspect of the present invention provides a process for the preparation of tofacitinib of Formula I

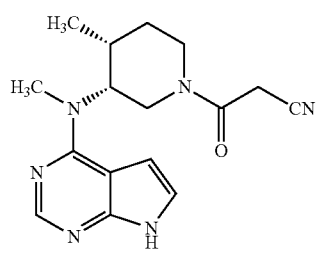

Formula I or isomers or a mixture of isomers or salts thereof, wherein the process comprises the steps of:

a) treating 3-bromo-4-methylpyridine with benzyl halide to obtain a compound of Formula II;

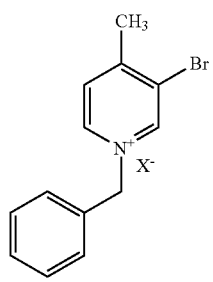

Formula II b) treating the compound of Formula II with methylamine to obtain a compound of Formula III;

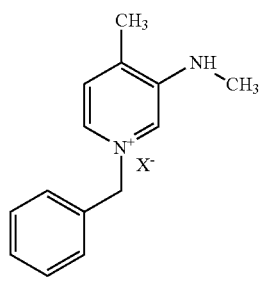

Formula III c) reducing the compound of Formula III to obtain a compound of Formula IV; and

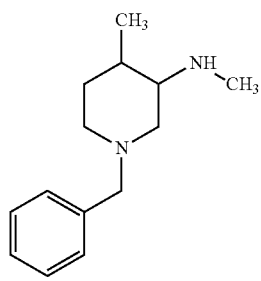

Formula IV d) converting the compound of Formula IV into tofacitinib of Formula I or isomers or a mixture of isomers or salts thereof, wherein X⁻ is Cl⁻, Br⁻, or I⁻.

A thirteenth aspect of the present invention provides a process for the preparation of tofacitinib of Formula I

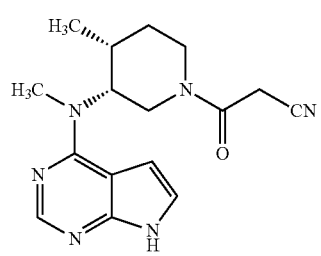

Formula I or isomers or a mixture of isomers or salts thereof wherein, the process comprises the steps of:

a) treating a compound of Formula II

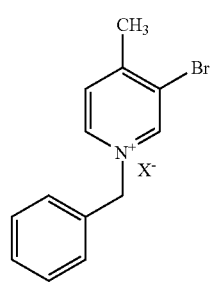

Formula II with methylamine to obtain a compound of Formula III;

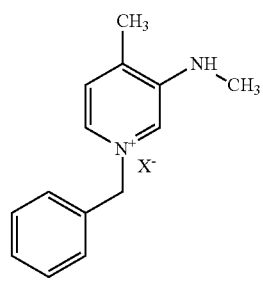

Formula III b) reducing the compound of Formula III to obtain a compound of Formula IV; and

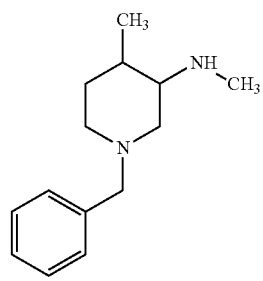

Formula IV c) converting the compound of Formula IV into tofacitinib of Formula I or isomers or a mixture of isomers or salts thereof, wherein X⁻ is Cl⁻, Br⁻, or I⁻.

A fourteenth aspect of the present invention provides a process for the preparation of tofacitinib of Formula I

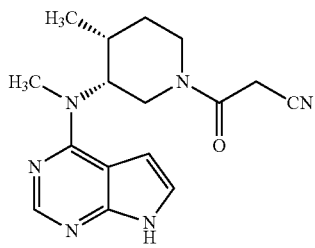
Formula I or isomers or a mixture of isomers or salts thereof, wherein the process comprises the steps of:
a) reducing a compound of Formula III

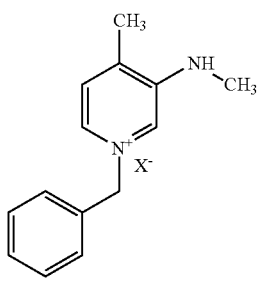
Formula III to obtain a compound of Formula IV; and

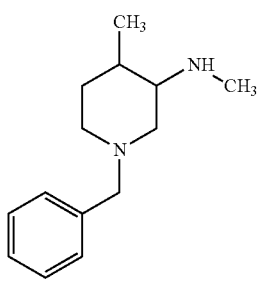
Formula IV b) converting the compound of Formula IV into tofacitinib of Formula I or isomers or a mixture of isomers or salts thereof,
wherein $X^-$ is $Cl^-$, $Br^-$, or $I^-$.

A fifteenth aspect of the present invention provides a process for the preparation of tofacitinib of Formula I

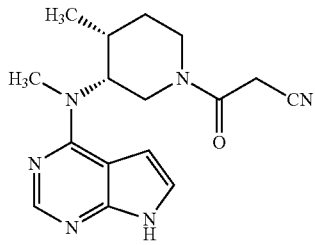
Formula I or isomers or a mixture of isomers or salts thereof, wherein the process comprises the steps of:
a) treating a compound of Formula V

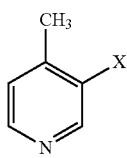
Formula V with benzyl halide to obtain a compound of Formula VI;

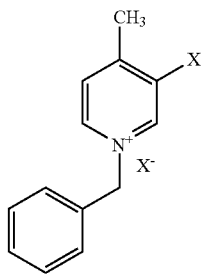
Formula VI b) treating the compound of Formula VI with methylamine to obtain a compound of Formula III;

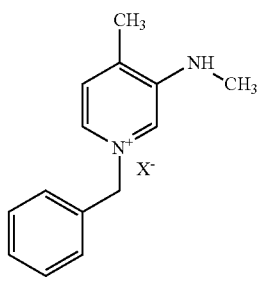
Formula III c) reducing the compound of Formula III to obtain a compound of Formula IV; and

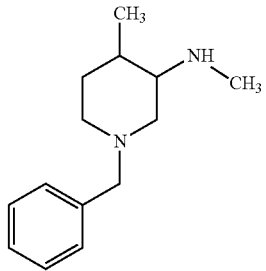
Formula IV d) converting the compound of Formula IV into tofacitinib of Formula I or isomers or a mixture of isomers or salts thereof,
wherein X is Cl, Br, or I, and $X^-$ is $Cl^-$, $Br^-$, or $I^-$.

A sixteenth aspect of the present invention provides a process for the preparation of tofacitinib of Formula I

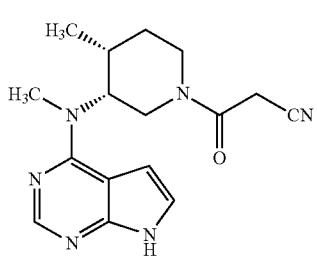
Formula I or isomers or a mixture of isomers or salts thereof, wherein the process comprises the steps of:

a) treating a compound of Formula VI

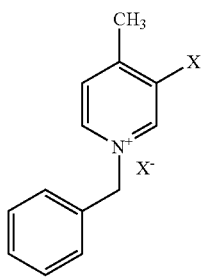

Formula VI with methylamine to obtain a compound of Formula III;

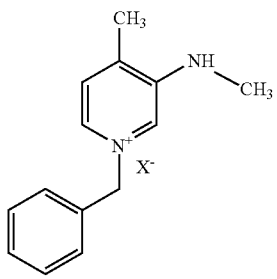

Formula III b) reducing the compound of Formula III to obtain a compound of Formula IV; and

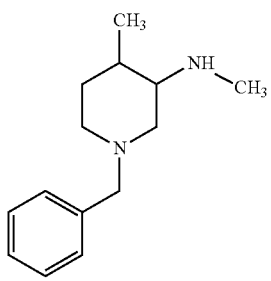

Formula IV c) converting the compound of Formula IV into tofacitinib of Formula I or isomers or a mixture of isomers or salts thereof, wherein X is Cl, Br, or I, and X⁻ is Cl⁻, Br⁻, or I⁻.

The compound of Formula V or 3-bromo-4-methylpyridine, can be prepared by any method provided in the prior art, for example, U.S. Pat. Nos. 7,456,192 and 5,733,912; Chinese Patent No. CN 100460394; or U.S. Publication No. 2007/0078135, or as described herein. The compound of Formula V or 3-bromo-4-methylpyridine is treated with a benzyl halide to obtain the compound of Formula VI or the compound of Formula II in a solvent. The benzyl halide is selected from the group comprising benzyl chloride, benzyl bromide, and benzyl iodide. The solvent is selected from the group comprising toluene, acetone, dichloromethane, tetrahydrofuran, ethanol, and mixtures thereof. The compound of Formula V or 3-bromo-4-methylpyridine is treated with the benzyl halide up to the reflux temperature of the solvent for about 2 hours to about 30 hours. The product may be isolated from the mixture by methods including cooling, decantation, filtration, concentration, chromatography, distillation, evaporation, centrifugation, or a combination thereof. The obtained mixture may further be dried.

The compound of Formula VI or the compound of Formula II is treated with methylamine to obtain the compound of Formula III in the optional presence of a catalyst. A solvent can also be used. Methylamine can be used in the form of a solution, for example, an aqueous solution or methanolic solution. The solvent is selected from the group comprising methanol, ethanol, propanol, and mixtures thereof. The catalyst is selected from the group comprising cuprous oxide, copper powder, cuprous iodide, and cuprous bromide. The compound of Formula VI or the compound of Formula II is treated with methylamine up to a temperature of 100° C. in a pressure vessel for about 2 hours to about 30 hours. The product may be isolated from the mixture by methods including cooling, decantation, filtration, concentration, chromatography, distillation, evaporation, centrifugation, or a combination thereof.

The compound of Formula III is reduced in the presence of a reducing agent to obtain the compound of Formula IV in a solvent. The reducing agent is selected from the group comprising sodium borohydride and potassium borohydride. The solvent is selected from the group comprising methanol, ethanol, propanol, water, and mixtures thereof. The compound of Formula III is reduced in the presence of the reducing agent at about 0° C. to about 50° C. for about 2 hours to about 30 hours. The product may be isolated from the mixture by methods including cooling, decantation, filtration, concentration, chromatography, distillation, evaporation, centrifugation, or a combination thereof, and may further be crystallized.

The compound of Formula IV prepared according to the process of the present invention may be converted into tofacitinib of Formula I

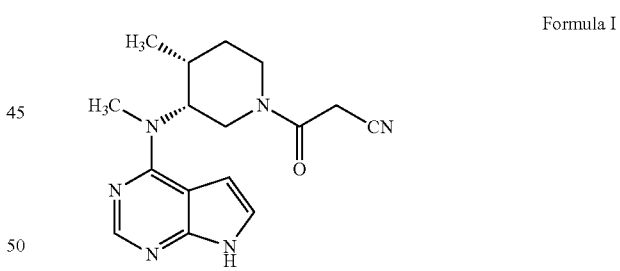

Formula I or isomers or a mixture of isomers thereof by following any method provided in the prior art, for example, by following Example 14 of U.S. Pat. No. RE41,783 or by following Example 6 of U.S. Pat. No. 7,301,023.

Tofacitinib of Formula I or isomers of tofacitinib or a mixture of isomers thereof may be converted into a salt by following any method provided in the prior art, for example, by following Example 1 of U.S. Pat. No. 6,965,027 or by following Example 1 or Example 8 of PCT Publication No. WO 2012/135338.

The term "about", as used herein, when used along values assigned to certain measurements and parameters means a variation of up to 10% from such values, or in case of a range of values, means up to a 10% variation from both the lower and upper limits of such ranges.

A seventeenth aspect of the present invention provides a compound of Formula II

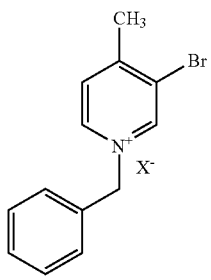

Formula II wherein X⁻ is Cl⁻, Br⁻, or I⁻.

An eighteenth aspect of the present invention provides a compound of Formula III

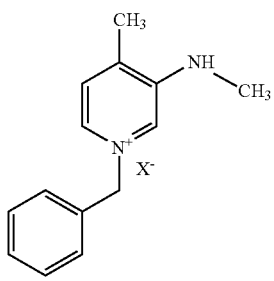

Formula III wherein X⁻ is Cl⁻, Br⁻, or I⁻.

A nineteenth aspect of the present invention provides a compound of Formula VI

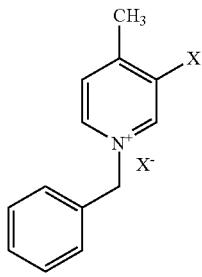

Formula VI wherein X is Cl, Br, or I, and X⁻ is Cl⁻, Br⁻, or I⁻.

A twentieth aspect of the present invention provides the use of a compound of Formula II

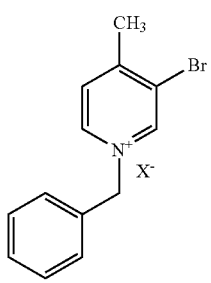

Formula II for the preparation of tofacitinib or isomers or a mixture of isomers or salts thereof,
wherein X⁻ is Cl⁻, Br⁻, or I⁻.

A twenty-first aspect of the present invention provides the use of a compound of Formula III

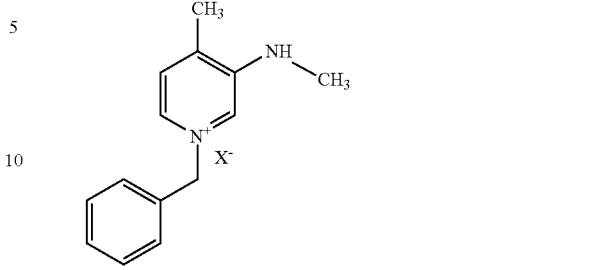

Formula III for the preparation of tofacitinib or isomers or a mixture of isomers or salts thereof, wherein X⁻ is Cl⁻, Br⁻, or I⁻.

A twenty-second aspect of the present invention provides the use of a compound of Formula VI

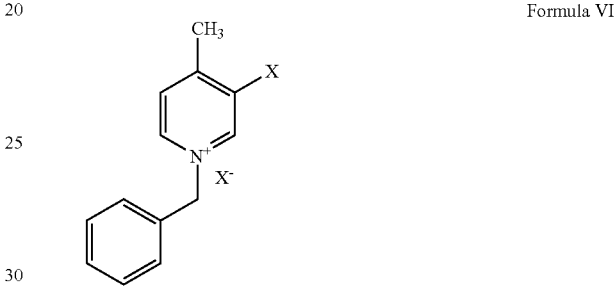

Formula VI for the preparation of tofacitinib or isomers or a mixture of isomers or salts thereof, wherein X is Cl, Br, or I, and X⁻ is Cl⁻, Br⁻, or I⁻.

Methods:

¹H NMR spectra were recorded on a Bruker® AVANCE III 400 MHz NMR spectrometer (Pulse length: 10.75 μsec; Power Level: 2.00 dB; Inter pulse delay: 6.50 μsec; Probe: 5 mm SE1 1H/D−; Sweep Width: 8223.685 Hz; Dwell time: 60.800 μsec). Mass analysis was performed on an Applied Biosystems® API 2000 triple quadrupole mass spectrometer by molecular weight in +ve ionization.

While the present invention has been described in terms of its specific embodiments, certain modifications and equivalents will be apparent to those skilled in the art and are intended to be included within the scope of the present invention.

EXAMPLES

Example 1

Preparation of 3-bromo-4-methylpyridine (Formula V, wherein X=Br)

4-Methylpyridine (50 g) was added slowly to aluminum chloride (182 g) with vigorous stirring under nitrogen over 1 hour. The resulting mixture was maintained at 95° C. to 105° C. and bromine (51 g) was introduced through the condenser over 5 hours. The reaction mixture was stirred at 95° C. to 105° C. for 15 hours. Additional bromine (32 g) was added to the reaction mixture over 3 hours and the reaction mixture was stirred for 20 hours at 95° C. to 105° C. The mixture was cooled to 25° C. to 30° C. and poured over crushed ice (1.3 kg) slowly with vigorous stirring. A saturated aqueous sodium hydroxide solution was added to the aqueous mixture until all the inorganic material was dissolved. The aqueous layer was extracted with dichloromethane (2×300 mL), and the combined organic layer was recovered under vacuum. The oil obtained was fractionally distilled under 13 mm pressure to obtain the title compound.
Yield=46 g (49%)

Example 2

Preparation of 1-benzyl-3-bromo-4-methylpyridinium bromide (Formula VI, wherein X=Br and X⁻=Br⁻ or Formula II, wherein X⁻=Br⁻)

Benzyl bromide (16.4 g) was added to a solution of 3-bromo-4-methylpyridine (Formula V, obtained according to Example 1, 15 g) in toluene (150 mL). The resulting mixture was heated to 110° C. and then maintained at 105° C. to 110° C. for 20 hours under inert atmosphere. The mixture was cooled to 5° C. and then maintained at 5° C. to 10° C. for 1 hour. The solid was filtered, washed with toluene (30 mL), and dried under vacuum at 50° C. to 55° C. for 10 hours.
Yield=25.95 g (87%)
Melting Point=205° C. to 208° C.
$^1$H NMR (CD$_3$OD, 400 MHz): 9.4 (1H, br), 8.9 (1H, d), 8.06 (1H, d), 7.4-7.5 (5H, m), 5.8 (2H, s), 2.7 (3H, s).
Mass (m/z): 263 [M$^+$]

The compounds of Formula VI or Formula II wherein X=Br and X⁻=Cl⁻ or I⁻, and the compounds of Formula VI, wherein X=Cl or I and X⁻=Br⁻, or I⁻, can be prepared by a method analogous to that as described in Example 2.

Example 3

Preparation of 1-benzyl-4-methyl-3-(methylamino)pyridinium bromide (Formula III, wherein X⁻=Br⁻)

Cuprous oxide (0.2 g) was added to a mixture of 1-benzyl-3-bromo-4-methylpyridinium bromide (Formula VI, obtained according to Example 2, 5 g) in methanolic methylamine solution (11.5%, 25 g) under nitrogen atmosphere. The reaction mixture was heated to 75° C. in an autoclave and maintained at this temperature for 24 hours. The solvent was recovered completely under vacuum to obtain a dark brown oily mass.
Yield=4.05 g (95%)
$^1$H NMR (CDCl$_3$, 400 MHz): 9.2 (1H, br), 8.7 (1H, br), 8.07 (1H, br), 7.6-7.7 (5H, m), 6.0 (2H, br), 2.84 (3H, s), 2.3 (3H, br).
Mass (m/z): 213[M$^+$]

The compounds of Formula III, wherein X⁻=Cl⁻ or I⁻, can be prepared by a method analogous to that as described in Example 3.

Example 4

Preparation of (1-benzyl-4-methylpiperidin-3-yl)-methylamine (Formula IV)

Sodium borohydride (7.28 g) was added to a cooled solution (0° C. to 5° C.) of 1-benzyl-4-methyl-3-(methylamino)pyridinium bromide (Formula III, obtained according to Example 3, 13 g) in ethanol (68 mL) and water (7.5 mL) at 0° C. to 5° C. over 30 minutes. The temperature of the reaction mass was raised to 25° C. and the reaction mixture was stirred for 20 hours at 20° C. to 25° C. Water (50 mL) was added to the resulting mass and it was filtered to remove inorganic salt. The filtrate was extracted with dichloromethane (2×100 mL) followed by the recovery of the solvent under vacuum at 35° C. to obtain a dark brown oily mass.

The oily mass was treated with 10% ethanolic hydrochloric acid and then crystallized in acetone to provide the title compound.
Yield=5.2 g (53.7%)

We claim:
1. A process for the preparation of a compound of Formula IV

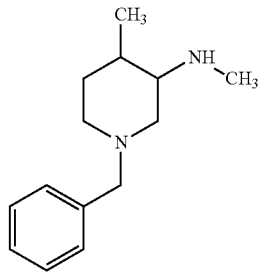

Formula IV wherein the process comprises reducing a compound of Formula III

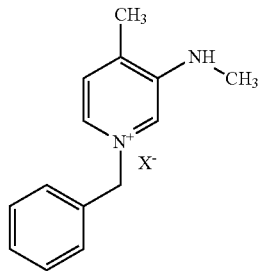

Formula III to obtain the compound of Formula IV,
wherein X⁻ is Cl⁻, Br⁻, or I⁻.

2. A process for the preparation of a compound of Formula III

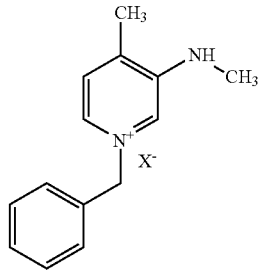

Formula III wherein X⁻ is Cl⁻, Br⁻, or I⁻
comprising
a) treating a compound of Formula V

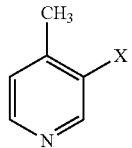

Formula V with a benzyl halide to obtain a compound of Formula VI

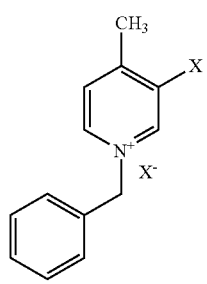

Formula VI wherein X is Cl, Br, or I, and X⁻ is Cl⁻, Br⁻, or I⁻, and
b) treating the compound of Formula VI with methylamine to obtain the compound of Formula III.

3. A process for the preparation of a compound of Formula III

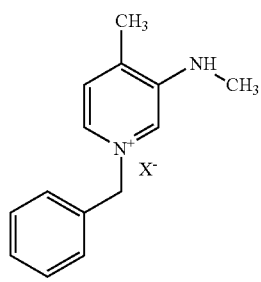

Formula III comprising treating a compound of Formula VI

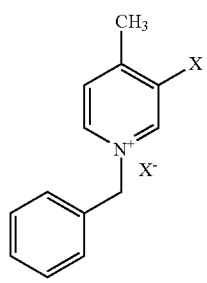

Formula VI with methylamine to obtain the compound of Formula III, wherein X is Cl, Br, or I, and X⁻ is Cl⁻, Br⁻, or I⁻.

4. The process according to claim 2, wherein the compound of Formula III is further reduced to obtain a compound of Formula IV

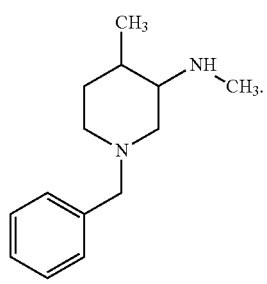

Formula IV

5. The process according to claim 3, wherein the compound of Formula III is further reduced to obtain a compound of Formula IV

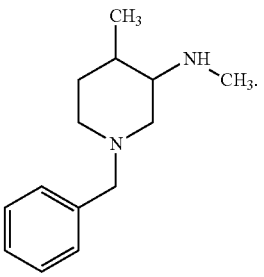

Formula IV

6. The process according to claim 1, wherein the compound of Formula IV is further converted into tofacitinib of Formula I

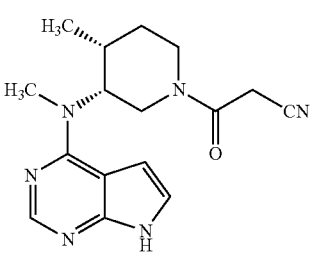

Formula I or salts thereof.

7. The process according to claim 4, wherein the compound of Formula IV is further converted into tofacitinib of Formula I

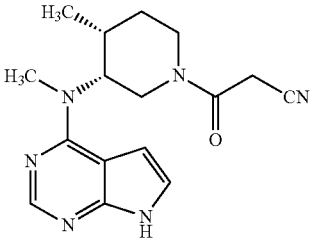

Formula I or salts thereof.

8. The process according to claim 5, wherein the compound of Formula IV is further converted into tofacitinib of Formula I

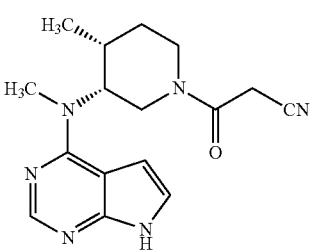

Formula I or salts thereof.

9. The process according to claim 2, wherein the benzyl halide is selected from the group comprising benzyl chloride, benzyl bromide, and benzyl iodide.

10. The process according to claim 2, wherein the compound of Formula V is treated with the benzyl halide in a solvent selected from the group comprising toluene, acetone, dichloromethane, tetrahydrofuran, ethanol, and mixtures thereof.

11. The process according to claim 3, wherein the compound of Formula VI is treated with methylamine in the presence of a catalyst.

12. The process according to claim 11, wherein the catalyst is selected from the group comprising cuprous oxide, copper powder, cuprous iodide, and cuprous bromide.

13. The process according to claim 2 or 3, wherein the compound of Formula VI is treated with methylamine in a solvent selected from the group comprising methanol, ethanol, propanol, and mixtures thereof.

14. The process according to claim 1, 4, or 5, wherein the reduction is carried out in the presence of a reducing agent selected from the group comprising sodium borohydride and potassium borohydride.

15. The process according to claim 1, 4, or 5, wherein the compound of Formula III is reduced to obtain the compound of Formula IV in a solvent selected from the group comprising methanol, ethanol, propanol, water, and mixtures thereof.

16. A compound of Formula III,

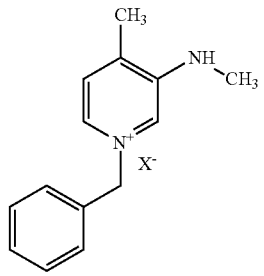

Formula III wherein $X^-$ is $Cl^-$, $Br^-$, or $I^-$.